US012569207B2

(12) United States Patent
Hattori et al.

(10) Patent No.: US 12,569,207 B2
(45) Date of Patent: Mar. 10, 2026

(54) DEVICE FOR INFERRING VIRTUAL MONOCHROMATIC X-RAY IMAGE, CT SYSTEM, METHOD OF CREATING TRAINED NEURAL NETWORK, AND STORAGE MEDIUM

(71) Applicants: GE Precision Healthcare LLC, Waukesha, WI (US); Kansai Medical University, Hirakata City (JP)

(72) Inventors: Miyo Hattori, Hino (JP); Yuri Teraoka, Hino (JP); Ayako Matsumi, Hino (JP); Yasuhiro Imai, Hino (JP); Yuhei Koike, Hirakata City (JP)

(73) Assignees: GE Precision Healthcare LLC, Waukesha, WI (US); Kansai Medical University, Hirakata City (JP)

( * ) Notice: Subject to any disclaimer, the term of this patent is extended or adjusted under 35 U.S.C. 154(b) by 203 days.

(21) Appl. No.: 18/456,884

(22) Filed: Aug. 28, 2023

(65) Prior Publication Data

US 2024/0065645 A1 Feb. 29, 2024

(30) Foreign Application Priority Data

Aug. 30, 2022 (JP) ................................. 2022-137324

(51) Int. Cl.
| | |
|---|---|
| *A61B 6/00* | (2024.01) |
| *A61B 6/03* | (2006.01) |
| *A61B 6/42* | (2024.01) |
| *A61B 6/46* | (2024.01) |

(52) U.S. Cl.
CPC ............ *A61B 6/032* (2013.01); *A61B 6/4208* (2013.01); *A61B 6/461* (2013.01); *A61B 6/482* (2013.01)

(58) Field of Classification Search
CPC ....... A61B 6/032; A61B 6/4208; A61B 6/461; A61B 6/482; A61B 6/481
See application file for complete search history.

(56) References Cited

U.S. PATENT DOCUMENTS

| | | | | |
|---|---|---|---|---|
| 2021/0110583 A1* | 4/2021 | Lee | ......................... | A61B 6/482 |
| 2023/0263492 A1* | 8/2023 | Yamazoe | .................. | G06T 5/00 600/408 |
| 2024/0070862 A1* | 2/2024 | Taguchi | .................. | A61B 6/461 |
| 2024/0185428 A1* | 6/2024 | Lilaonitkul | ............... | G06T 7/11 |
| 2024/0237956 A1* | 7/2024 | Gong | ..................... | A61B 6/032 |

FOREIGN PATENT DOCUMENTS

| | | | | |
|---|---|---|---|---|
| CN | 110544282 A | * | 12/2019 | ........... G06N 3/0454 |

OTHER PUBLICATIONS

Translation of CN 110544282 A (Year: 2019).*

* cited by examiner

*Primary Examiner* — David J Makiya
*Assistant Examiner* — Mamadou Faye

(57) ABSTRACT

Systems and methods are described, which generate a plurality of virtual monochromatic X-ray images having different energy levels even with a CT system with single energy CT. An example CT system includes an X-ray tube in which a prescribed tube voltage (120 (kVp)) is applied and one or more processors. The one or more processors perform an operation including inputting a CT image generated based on the single energy CT data collected from a subject body to a trained neural network (94), and causing the trained neural network to infer 40 (keV), 50 (keV), 60 (keV), 80 (keV), 90 (keV), and 100 (keV) virtual monochromatic X-ray images based on the CT image.

16 Claims, 17 Drawing Sheets

(120kVp)

11

70

DEVICE FOR INFERRING VIRTUAL MONOCHROMATIC X-RAY IMAGE, CT SYSTEM, METHOD OF CREATING TRAINED NEURAL NETWORK, AND STORAGE MEDIUM

CROSS-REFERENCE TO RELATED APPLICATIONS

This application claims priority to Japanese Application No. 2022-137324, filed on Aug. 30, 2022, the disclosure of which is incorporated herein by reference in its entirety.

TECHNICAL FIELD

The present invention relates to a device for inferring a virtual monochromatic X-ray image, a CT system for inferring a virtual monochromatic X-ray image, a method of creating a trained neural network for inferring a virtual monochromatic X-ray image, and a storage medium in which a command for inferring a virtual monochromatic X-ray image is stored.

BACKGROUND ART

A CT system is known as a medical device that noninvasively images a subject body. CT systems are widely used in hospitals and other medical facilities because they can acquire tomographic images of a subject body in a short scanning time.

The CT system applies a prescribed voltage to the cathode-anode tube of an X-ray tube to generate X-rays. The generated X-rays penetrate the specimen and are detected by the detector. The CT system reconstructs a CT image of the subject body based on data detected by the detector.

SUMMARY

Single energy CT (SECT) is a well-known imaging technique for CT systems. Single energy CT is a method of obtaining a CT image of a subject body by applying a prescribed voltage (for example, 120 kVp) to a cathode-anode tube of an X-ray tube to generate X-rays. However, with single energy CT, the CT values may be close even for different materials, making it difficult to detect a lesion, for example.

On the other hand, dual energy CT (DECT) technology is being researched and developed. Dual energy CT is a technique that uses X-rays in different energy regions to distinguish materials, and dual-energy CT-compatible CT systems are commercially available. The dual energy CT technique has a wide range of applications, and can produce virtual monochromatic X-ray images at various energy levels, for example. The accuracy of lesion detection can be improved by comparing virtual monochromatic X-ray images of different energy levels; therefore, an increasing number of medical institutions are introducing dual energy CT.

However, dual energy CT devices are generally more expensive than single energy CT devices, and although some medical institutions have introduced CT systems compatible with single energy CT, many medical institutions have not introduced CT systems compatible with dual energy CT. Therefore, there is a need for a technology that can generate a plurality of virtual monochromatic X-ray images having different energy levels even when using a CT system with single energy CT.

A first aspect of the present invention is a device, including one or more processors for performing an operation. The operation includes inputting a CT image generated based on single energy CT data collected from a subject body into a trained neural network, the trained neural network being generated by a neural network performing training using training data in the training phase, the training data including a plurality of virtual monochromatic X-ray images generated based on dual energy CT data and having mutually different energy levels, the plurality of virtual monochromatic X-ray images including a first virtual monochromatic X-ray image with an energy level corresponding to the tube voltage of a CT system collecting single energy CT data and a first set of two or more virtual monochromatic X-ray images having mutually different energy levels, and in the training phase, the neural network performing learning with the training data such that the first virtual monochromatic X-ray image is used as input to the neural network and the first set of two or more virtual monochromatic X-ray images are output from the neural network, and causing the trained neural network to infer a second set of a plurality of two or more virtual monochromatic X-ray images having different energy levels based on the input CT image.

A second aspect of the present invention is a CT system for collecting single energy CT data, including an X-ray tube to which a prescribed tube voltage is applied; and one or more processors. The one or more processors performs an operation, the operation including generating a CT image based on single energy CT data collected from a subject body, inputting the CT image to a trained neural network, the trained neural network being generated by a neural network performing learning using training data in the training phase, the training data including a plurality of virtual monochromatic X-ray images generated based on dual energy CT data and having mutually different energy levels, the plurality of virtual monochromatic X-ray images including a first virtual monochromatic X-ray image with an energy level corresponding to the prescribed tube voltage and a first set of two or more virtual monochromatic X-ray images having mutually different energy levels, and in the training phase, the neural network performing learning with the training data such that the first virtual monochromatic X-ray image is used as input to the neural network and the first set of two or more virtual monochromatic X-ray images are output from the neural network, and causing the trained neural network to infer a second set of two or more virtual monochromatic X-ray images having different energy levels based on the input CT image.

A third aspect of the present invention is a method of creating a trained neural network, including the step of a neural network performing learning using training data, the training data including a plurality of virtual monochromatic X-ray images generated based on dual energy CT data and having mutually different energy levels, the plurality of virtual monochromatic X-ray images including a first virtual monochromatic X-ray image with an energy level corresponding to the tube voltage of a CT system collecting single energy CT data and a first set of two or more virtual monochromatic X-ray images having mutually different energy levels, and the neural network performing learning with the training data such that the first virtual monochromatic X-ray image is used as input to the neural network and the first set of two or more virtual monochromatic X-ray images are output from the neural network.

A fourth aspect of the present invention is a storage medium, which is one or more non-transitory computer-readable recording media in which one or more command executable by one or more processor is stored, wherein the one or more command causes the one or more processor to perform an operation. The operation includes inputting a CT image generated based on single energy CT data collected from a subject body into a trained neural network, the trained neural network being generated by a neural network performing learning using training data in the training phase, the training data including a plurality of virtual monochromatic X-ray images generated based on dual energy CT data and having mutually different energy levels, the plurality of virtual monochromatic X-ray images including a first virtual monochromatic X-ray image with an energy level corresponding to the tube voltage of a CT system collecting single energy CT data and a first set of two or more virtual monochromatic X-ray images having mutually different energy levels, and in the training phase, the neural network performing learning with the training data such that the first virtual monochromatic X-ray image is used as input to the neural network and the first set of two or more virtual monochromatic X-ray images are output from the neural network, and causing the trained neural network to infer a second set of a plurality of two or more virtual monochromatic X-ray images having different energy levels based on the input CT image.

In the present invention, a neural network is trained with a plurality of virtual monochromatic X-ray images generated based on dual energy CT data to create a trained neural network. Specifically, a neural network is trained with training data such that a first virtual monochromatic X-ray image having an energy level corresponding to the tube voltage of a CT system collecting single energy CT data is used as an input of the neural network and a first set of two or more virtual monochromatic X-ray images having mutually different energy levels are output from the neural network, to create a trained neural network.

Thus, in the present invention, the first virtual monochromatic X-ray image used as input for the neural network is a virtual monochromatic X-ray image having an energy level corresponding to the tube voltage of the CT system. Therefore, by inputting a CT image obtained by the CT system into the trained neural network, a virtual monochromatic X-ray image of sufficient quality can be inferred. Furthermore, the trained neural network infers two or more virtual monochromatic X-ray images having different energy levels, and thus can obtain virtual monochromatic X-ray images with optimal contrast for clinical purposes from the inferred two or more virtual monochromatic X-ray images, even in medical institutions where only CT systems with single energy CT have been installed.

DETAILED DESCRIPTION

An embodiment for carrying out the invention will be described below, but the present invention is not limited to the following embodiment.

Figure 1:
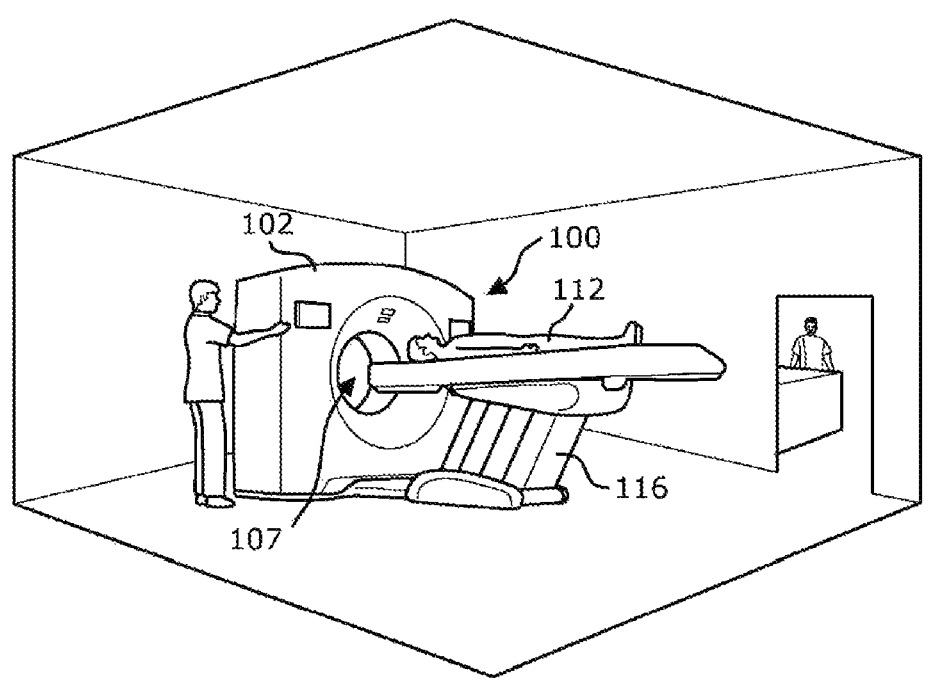
FIG. 1 is a perspective view of the CT system 100 of Embodiment 1.

FIG. 1 is a perspective view of a CT system 100 of Embodiment 1. The CT system 100 has a gantry 102. The gantry 102 has an opening 107. A subject body 112 is transported through the opening 107, and the subject body 112 can be scanned.

Figure 2:
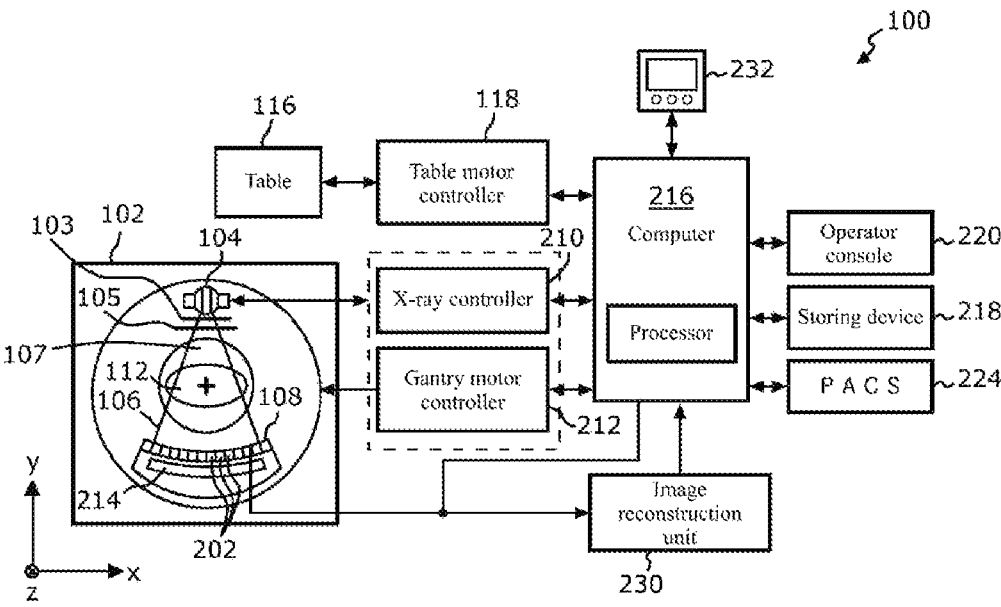
FIG. 2 is a block diagram of the CT system 100.

FIG. 2 is a block diagram of the CT system 100. The gantry 102 is equipped with an X-ray tube 104, a filter part 103, a front collimator 105, and a detector array 108. The X-ray tube 104 generates X-rays when a prescribed voltage (e.g., 120 kVp) is applied to the cathode-anode tube. The filter part 103 includes, for example, a flat plate filter and/or a bow-tie filter. The front collimator 105 is a component that narrows the X-ray irradiation range so that X-rays are not emitted in unwanted areas.

The detector array 108 includes a plurality of detector elements 202. A plurality of detector elements 202 detect the X-ray beam 106 that is emitted from the X-ray tube 104 and passes through the subject body 112 serving as an imaging target. Thus, the detector array 108 can acquire projection data for each view.

The projection data detected by the X-ray detector 108 is collected by the DAS 214. The DAS 214 performs prescribed processing, including sampling and digital conversion, on the collected projection data. The processed projection data is transmitted to a computer 216. The computer 216 stores the data from the DAS 214 in a storage device 218. The storage device 218 includes one or more storage media that store programs and instructions to be executed by the processor. The storage medium can be, for example, one or more non-transitory, computer-readable storage media. Storage devices 218 may include, for example, hard disk drives, floppy disk drives, compact disc read/write (CD-R/W) drives, digital versatile disk (DVD) drives, flash drives, and/or solid-state storage drives.

The computer 216 includes one or a plurality of processors. The computer 216 uses one or a plurality of processors to output commands and parameters to the DAS 214, X-ray controller 210, and/or gantry motor controller 212, to control system operations such as data acquisition and/or processing.

An operator console 220 is linked to the computer 216. An operator can enter prescribed operator inputs related to the operation of the CT system 100 into the computer 216 by operating the operator console 220. The computer 216 receives operator input, including commands and/or scan parameters, via the operator console 220 and controls system operation based on that operator input. The operator console 220 can include a keyboard (not shown) or touch screen for the operator to specify commands and/or scan parameters.

The X-ray controller 210 controls the X-ray tube 104 based on a signal from the computer 216. In addition, the gantry motor controller 212 controls the gantry motor based on a signal from the computer 216. FIG. 2 illustrates only one operator console 220, but two or more operator consoles may be linked to the computer 216. In addition, the CT system 100 may also allow a plurality of remotely located displays, printers, workstations and other devices to be coupled via, for example, wired and/or wireless networks.

In one embodiment, for example, the CT system 100 may include a Picture Archiving and Communication System (PACS) 224, or may be linked to a PACS 224. In a typical implementation, a PACS 224 can be coupled to a remote system such as a radiology department information system, hospital information system, and/or internal or external network (not depicted).

The computer 216 supplies commands to the table motor controller 118 to control the table 116. The table motor controller 118 can control the table 116 based on commands received. In particular, the table motor controller 118 can move the table 116 so that the subject body 112 is properly positioned within the opening 107 of the gantry 102.

As mentioned above, the DAS 214 samples and digitally converts the projection data acquired by the detector elements 202. The image reconstruction unit 230 then reconstructs the image using the sampled and digitally converted data. The image reconstruction unit 230 includes one or a plurality of processors, which can perform the image reconstruction process. In FIG. 2, the image reconstruction unit 230 is illustrated as a separate structural element from the computer 216, but the image reconstruction unit 230 may form a part of the computer 216. In addition, the computer 216 may also perform one or more functions of the image reconstruction unit 230. In addition, the image reconstruction unit 230 may be located away from the CT system 100 and operatively connected to the CT system 100 using a wired or wireless network.

The image reconstruction unit 230 can store the reconstructed image in the storage device 218. The image reconstruction unit 230 may also transmit the reconstructed image to the computer 216. The computer 216 can transmit the reconstructed image and/or patient information to a display part 232 communicatively coupled to the computer 216 and/or image reconstructor 230.

The computer 216 and/or image reconstructor 230 forms a device that performs processing of data collected by scanning the subject body, a device that performs various processes based on data received from the operator console 220, and a device that performs various processes based on data received from various controllers (118, 210, 212, and the like).

Note that at least some of the processing performed by the computer 216 and/or image reconstructor 230 may be performed by an external device that is separate from the CT system 100.

The various methods and processes described in the present specification can be stored as executable instructions on a non-transitory storage medium within the CT system 100. The executable instructions may be stored on a single storage medium or distributed across multiple storage mediums. One or more processors provided in the CT system 100 execute the various methods, steps, and processes described in the present specifications in accordance with instructions stored on a storage medium.

The CT system 100 is configured as described above. The CT system 100 is a device for acquiring a CT image of a subject body by applying a prescribed voltage (for example, 120 kVp) to a cathode-anode tube of an X-ray tube to generate X-rays. Therefore, the CT system 100 is a device for collecting single energy CT data.

On the other hand, dual energy CT (DECT) technology is being researched and developed. Dual energy CT is a technique that uses X-rays in different energy regions to distinguish materials, and dual-energy CT-compatible CT systems are commercially available. The dual energy CT technique has a wide range of applications, and can produce a plurality of virtual monochromatic X-ray images having different energy levels, for example. The accuracy of lesion detection can be improved by comparing a plurality of virtual monochromatic X-ray images having different energy levels; therefore, an increasing number of medical institutions are introducing dual energy CT.

However, dual energy CT devices are generally more expensive than single energy CT devices, and although some medical institutions have introduced CT systems compatible with single energy CT, many medical institutions have not introduced CT systems compatible with dual energy CT. Therefore, there is a need for a technology that can generate a plurality of virtual monochromatic X-ray images having different energy levels even for medical institutions only having single energy CT.

Therefore, the inventors of the present application, through extensive studies, conceived a method of generating a plurality of virtual monochromatic X-ray images having different energy levels based on single energy CT data. In the present embodiment, the basic concept for generating a plurality of virtual monochromatic X-ray images having different energy levels based on single energy CT data will be described below with reference to FIG. 3.

Figure 3:
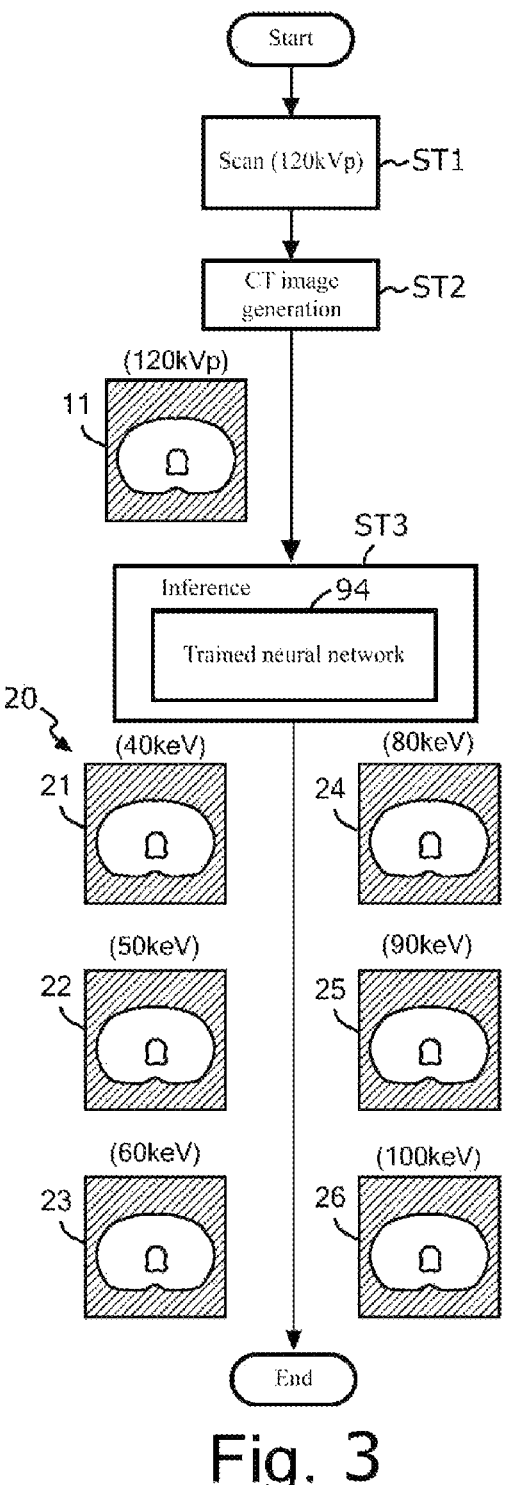
FIG. 3 is a flow diagram for describing a basic concept of a method of generating a plurality of virtual monochromatic X-ray images having different energy levels in Embodiment 1.

FIG. 3 is a flow diagram describing the basic concept of the method of generating a plurality of virtual monochromatic X-ray images having different energy levels in Embodiment 1. In step ST1, the subject body is scanned using a CT system that performs single energy CT imaging. In Embodiment 1, the tube voltage of the CT system is 120 kVp. In step ST2, a CT image 11 is generated based on data acquired by scanning the subject body using the CT system with a tube voltage of 120 kVp.

In step ST3, the CT image 11 obtained in step ST2 is input to a trained neural network 94 to infer a set 20 of a plurality of virtual monochromatic X-ray images 21 to 26. The plurality of virtual monochromatic X-ray images are a plurality of virtual monochromatic X-ray images having different energy levels. In FIG. 3, as an example of the plurality of virtual monochromatic X-ray images, a 40 (keV) virtual monochromatic X-ray image 21, a 50 (keV) virtual monochromatic X-ray image 22, a 60 (keV) virtual monochromatic X-ray image 23, an 80 (keV) virtual monochromatic X-ray image 24, a 90 (keV) virtual monochromatic X-ray image 25, and a 100 (keV) virtual monochromatic X-ray image 26 are depicted.

In Embodiment 1, the CT image 11 acquired by single energy CT imaging is input to the trained neural network 94. The trained neural network 94 infers the plurality of virtual monochromatic X-ray images 21 to 26 having mutually different energy levels based on the CT image 11. Therefore, even in medical institutions only having a CT system with single energy CT, virtual monochromatic X-ray images of various energy levels can be generated, and thus virtual monochromatic X-ray images of optimal contrast for clinical purposes can be obtained from the inferred virtual monochromatic X-ray images 21 to 26.

Figure 4:
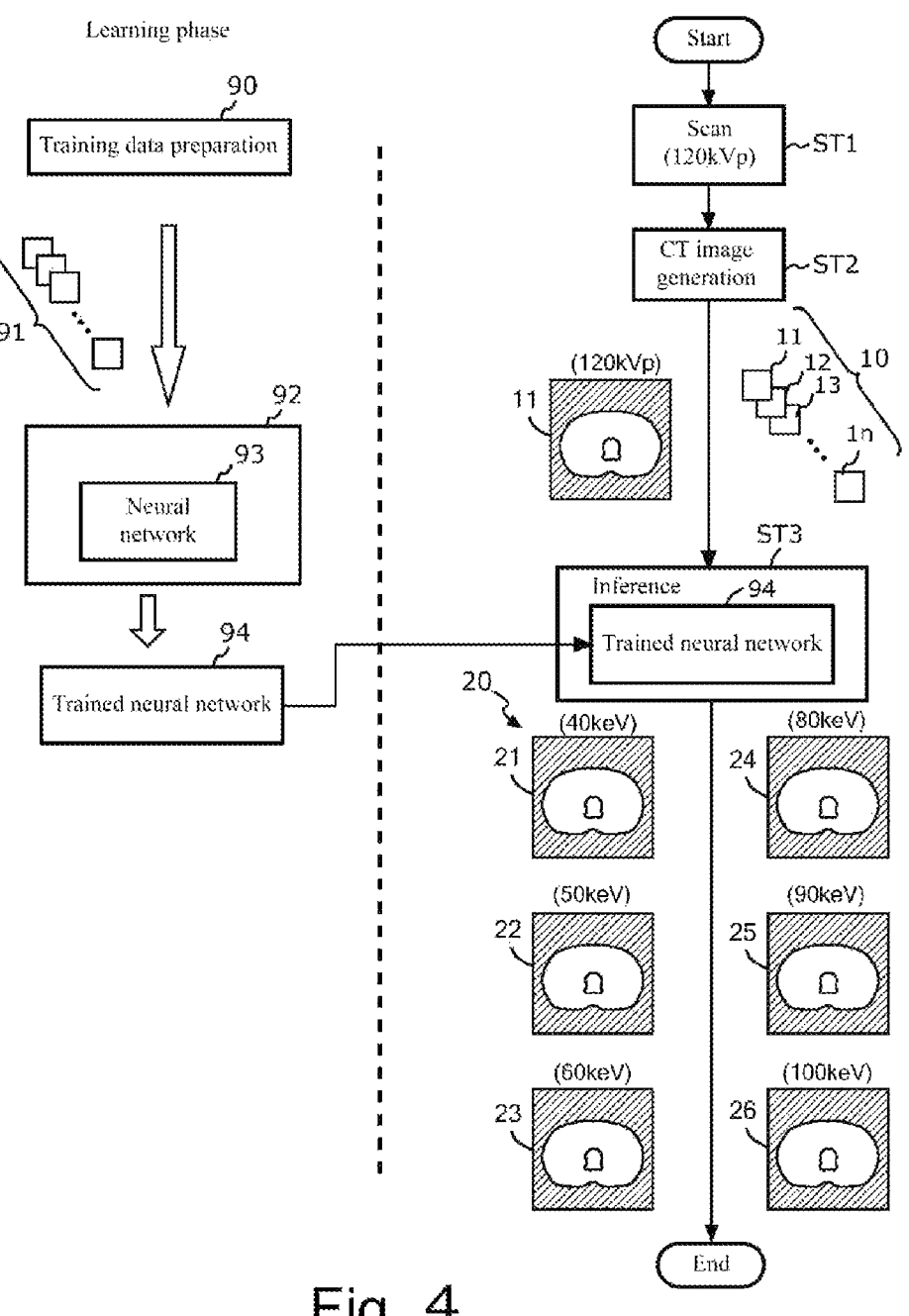
FIG. 4 is a flow diagram of performing a scan of a subject body and inferring a plurality of virtual monochromatic X-ray images using the CT system 100.

The following is a specific description of a method of acquiring a plurality of virtual monochromatic X-ray images having different energy levels in accordance with the technique described above, with reference to FIG. 4. FIG. 4 is a flow diagram of performing a scan of the subject body and inferring the plurality of virtual monochromatic X-ray images using the CT system 100. Embodiment 1 describes an example in which a contrast-enhanced CT scan, in which a contrast agent is injected into the subject body and the subject body is imaged, is performed as a scan of the subject body.

Note that as described with reference to FIG. 3, in Embodiment 1, a plurality of virtual monochromatic X-ray images having different energy levels are inferred based on the CT image 11 of single energy CT, and thus the trained neural network 94 capable of performing the inference must be prepared in advance. Therefore, the following describes the training phase in which the trained neural network 94 is created. Furthermore, after describing the training phase, the flow of inferring the plurality of virtual monochromatic X-ray images having different energy levels based on a CT image of single energy CT will be described.

Figure 5:
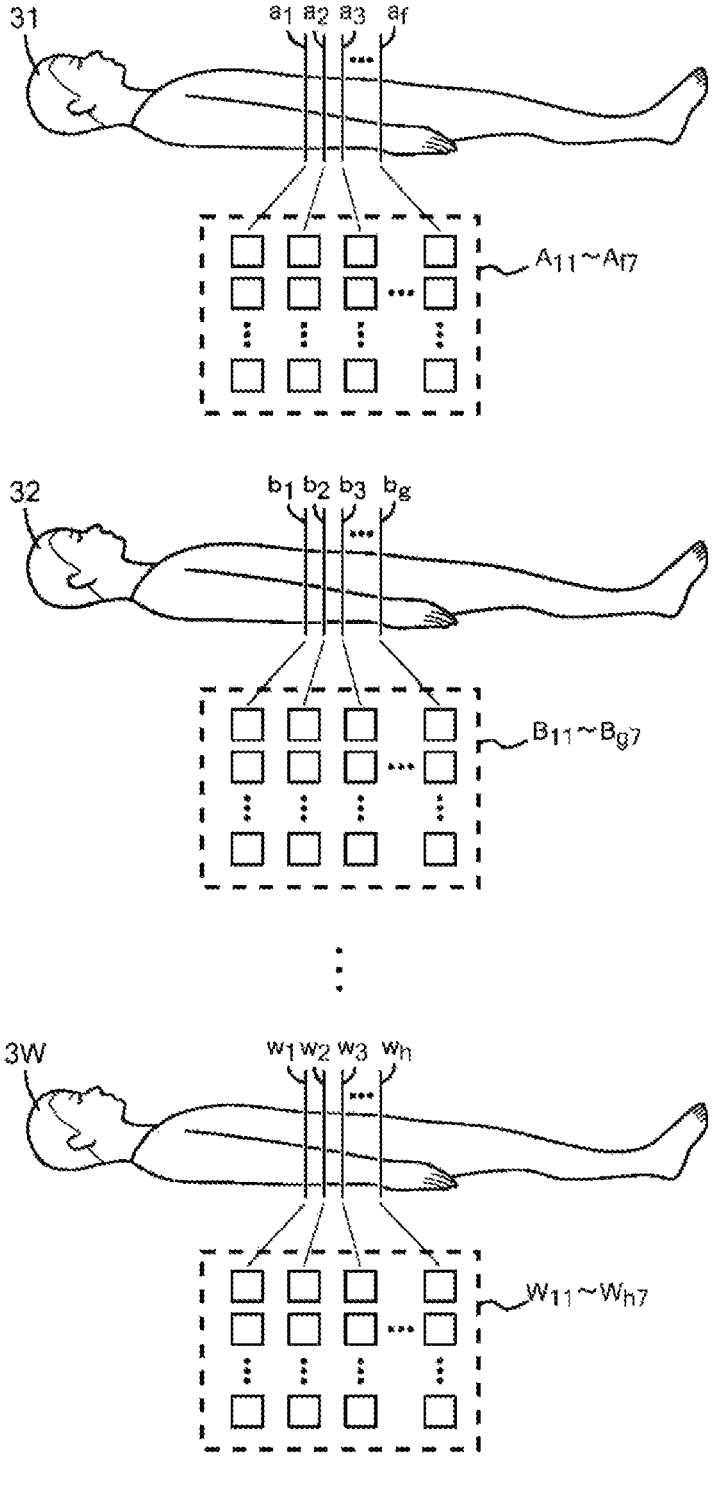
FIG. 5 is an explanatory diagram of training data.

In the training phase, the training data is first prepared in step ST90. FIG. 5 is an explanatory diagram of training data. Training data can be obtained from hospitals and other medical institutions. For example, a virtual monochromatic X-ray image obtained by actually scanning a patient at a medical institution can be prepared as training data. Note, as described above, Embodiment 1 is thought to perform a contrast-enhanced CT scan on the subject body. Therefore, in Embodiment 1, virtual monochromatic X-ray images obtained by contrast-enhanced CT scanning a patient at a medical institution such as a hospital or the like are prepared as training data. FIG. 5 depicts an example of preparing virtual monochromatic X-ray images obtained by performing contrast-enhanced CT scans on patients 31 to 3W at a hospital or other medical institution as training data. These virtual monochromatic X-ray images are generated based on dual energy CT data. First, a virtual monochromatic X-ray image acquired from the patient 31 is described.

Figure 6:
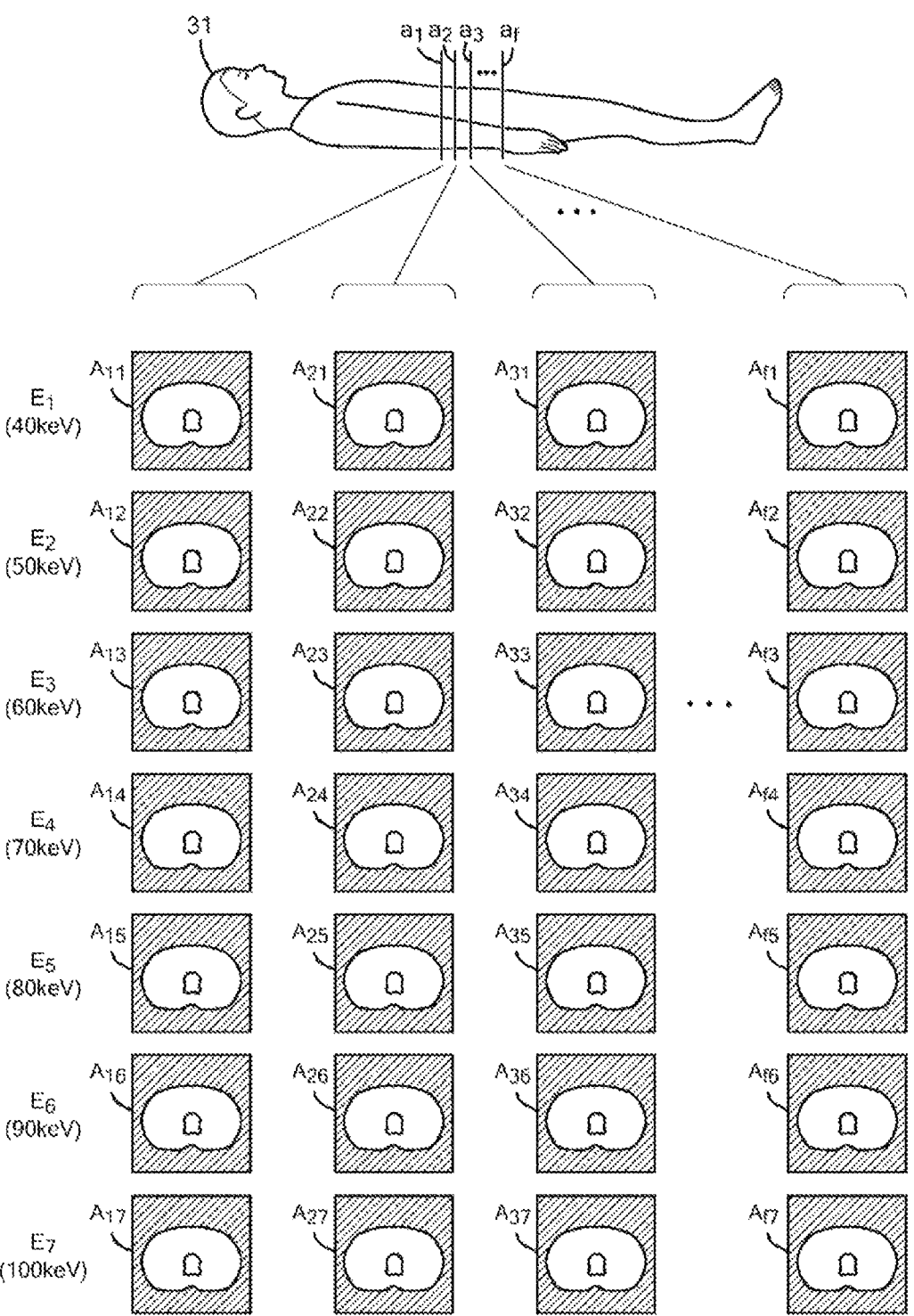
FIG. 6 is an explanatory diagram of a virtual monochromatic X-ray image acquired from a patient 31.

FIG. 6 is an explanatory diagram of virtual monochromatic X-ray images acquired from the patient 31. Although the virtual monochromatic X-ray images obtained from the patient 31 include virtual monochromatic X-ray images acquired at various time phases, for the sake of explanation, a plurality of virtual monochromatic X-ray images A11 to Af7 acquired at a prescribed time phase (e.g., arterial phase) are considered as virtual monochromatic X-ray images obtained from the patient 31.

Referring to slice a1, the plurality of virtual monochromatic X-ray images A11 to A17 are acquired in the slice a1. The virtual monochromatic X-ray images A11 to A17 are generated based on dual energy CT data and are virtual monochromatic X-ray images having mutually different energy levels. Specifically, they are as follows.

$A_{11}$: Virtual monochromatic X-ray image at energy level E1 (=40 (keV))

$A_{12}$: Virtual monochromatic X-ray image at energy level E2 (=50 (keV))

$A_{13}$: Virtual monochromatic X-ray image at energy level E3 (=60 (keV))

$A_{14}$: Virtual monochromatic X-ray image at energy level E4 (=70 (keV))

$A_{15}$: Virtual monochromatic X-ray image at energy level E5 (=80 (keV))

$A_{16}$: Virtual monochromatic X-ray image at energy level E6 (=90 (keV))

$A_{17}$: Virtual monochromatic X-ray image at energy level E7 (=100 (keV))

Furthermore, referring to a slice a2, a plurality of virtual monochromatic X-ray images $A_{21}$ to $A_{27}$ are acquired in the slice a2. The virtual monochromatic X-ray images $A_{21}$ to $A_{27}$ are generated based on dual energy CT data and are virtual monochromatic X-ray images having mutually different energy levels. Specifically, they are as follows.

$A_{21}$: Virtual monochromatic X-ray image at energy level E1 (=40 (keV))

$A_{22}$: Virtual monochromatic X-ray image at energy level E2 (=50 (keV))

$A_{23}$: Virtual monochromatic X-ray image at energy level E3 (=60 (keV))

$A_{24}$: Virtual monochromatic X-ray image at energy level E4 (=70 (keV))

$A_{25}$: Virtual monochromatic X-ray image at energy level E5 (=80 (keV))

$A_{26}$: Virtual monochromatic X-ray image at energy level E6 (=90 (keV))

$A_{27}$: Virtual monochromatic X-ray image at energy level E7 (=100 (keV))

In the same manner below, a plurality of virtual monochromatic X-ray images of energy levels E1 to E7 are acquired in other slices a3 to af. Therefore, a plurality of virtual monochromatic X-ray images $A_{11}$ to $A_{f7}$ are acquired from the patient 31. Furthermore, as depicted in FIG. 5, a plurality of virtual monochromatic X-ray images are acquired for the other patients 32 to 3W, as well as the patient 31. For example, virtual monochromatic X-ray images $B_{11}$ to $B_{g7}$ are obtained from the patient 32, and virtual monochromatic X-ray images $W_{11}$ to $W_{h7}$ are obtained from the patient 3W. Returning to FIG. 4, the description is continued.

Therefore, in step ST90, the virtual monochromatic X-ray images of energy levels E1 to E7 obtained from the patients 31 to 3W are prepared as training data 91. Note that the energy level of the virtual monochromatic X-ray image is not limited to the energy levels E1 to E7 above, but can be different from the energy levels E1 to E7. Furthermore, the example above describes a case in which actual virtual monochromatic X-ray images acquired from the patients 31 to 3W are used as training data. However, prescribed pre-processing may be performed on the actual virtual monochromatic X-ray images acquired from the patients 31 to 3W, and the virtual monochromatic X-ray images after pre-processing has been performed may be used as training data.

After preparing the training data 91, the flow proceeds to step 92. In step ST92, a training device (not depicted) performs training of the neural network 93 using the training data 91 to create the trained neural network 94. The following describes a training method of the neural network 93.

Figure 7:
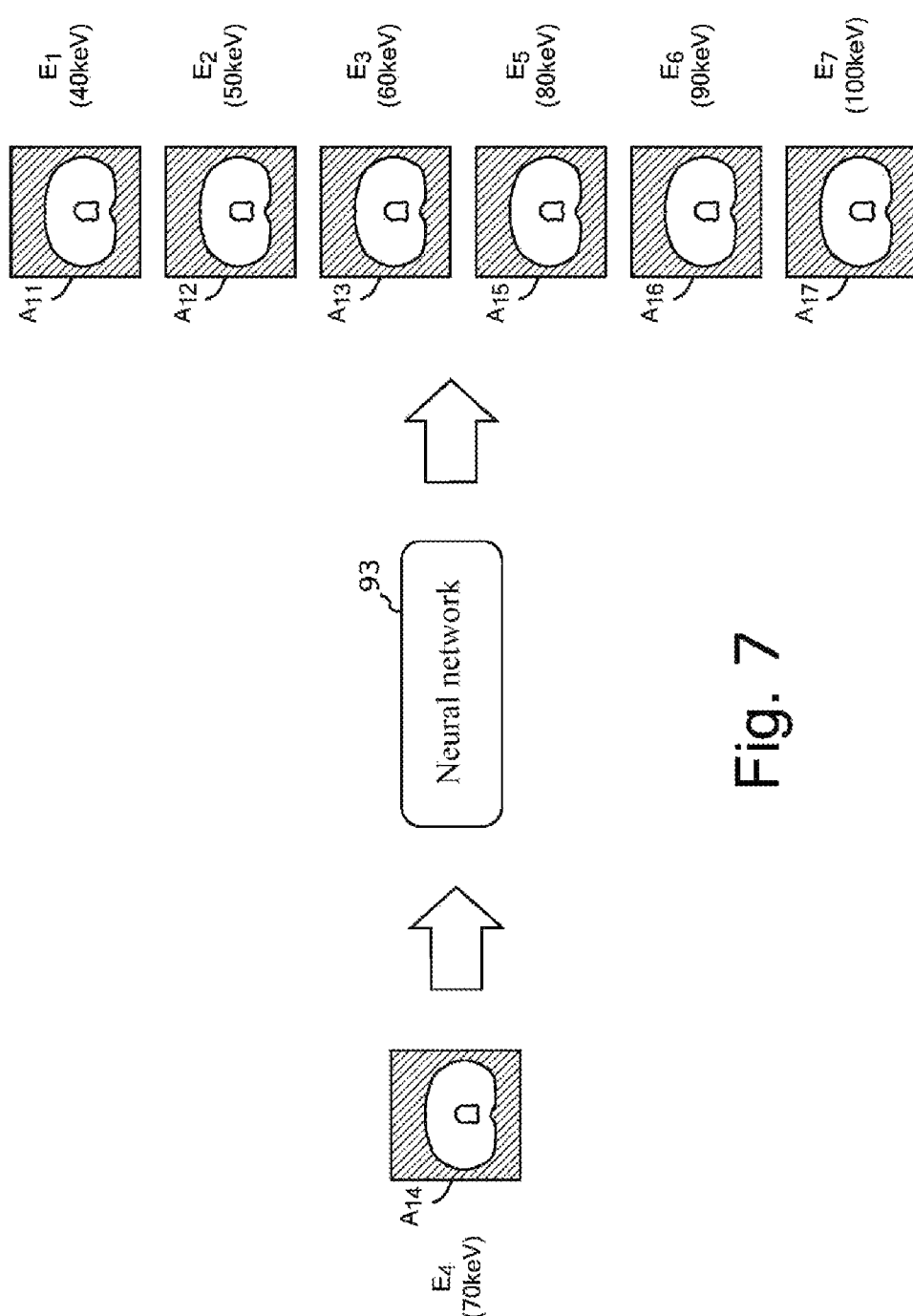
FIG. 7 is an explanatory diagram of a training method of a neural network 93.

FIG. 7 is an explanatory diagram of the training method of the neural network 93. First, the training is performed using the plurality of virtual monochromatic X-ray images $A_{11}$ to $A_{17}$ (see FIG. 6) obtained from the slice a1 of the patient 31. Specifically, training of the neural network 93 is performed such that the virtual monochromatic X-ray image $A_{14}$ having an energy level of 70 (keV) is used as an input of the neural network 93 and the virtual monochromatic X-ray images $A_{11}$, $A_{12}$, $A_{13}$, $A_{15}$, $A_{16}$, and $A_{17}$ having other energy levels (40 (keV), 50 (keV), 60 (keV), 80 (keV), 90 (keV), and 100 (keV)) are output from the neural network 93. Note that the reason for using the virtual monochromatic X-ray image $A_{14}$ having an energy level of 70 (keV) as an input of the neural network 93 is as follows.

In Embodiment 1, the tube voltage of the CT system 100 used for actually scanning the subject body 112 in step ST1 is 120 kVp, as described with reference to FIG. 3. Furthermore, the CT image 11 (see FIG. 3) that is input to the trained neural network 94 is generated based on the data obtained by scanning the subject body at a tube voltage of 120 kVp. Therefore, during the training phase, it is desirable to use a virtual monochromatic X-ray image corresponding to the energy level of X-rays at a tube voltage of 120 kVp, as an input of the neural network 93. The energy level of a virtual monochromatic X-ray image corresponding to a tube voltage of 120 kVp is, for example, E4=70 (keV). For this reason, in Embodiment 1, the virtual monochromatic X-ray image $A_{14}$ of 70 (keV) is used as an input of the neural network 93.

Therefore, the plurality of virtual monochromatic X-ray images $A_{11}$ to $A_{17}$ include the virtual monochromatic X-ray image $A_{14}$ having an energy level corresponding to a tube voltage of 120 kVp and six virtual monochromatic X-ray images $A_{11}$, $A_{12}$, $A_{13}$, $A_{15}$, $A_{16}$, and $A_{17}$ having mutually different energy levels. Furthermore, the neural network 93 performs learning using the virtual monochromatic X-ray images $A_{11}$ to $A_{17}$ such that the virtual monochromatic X-ray image $A_{14}$ is used as an input of the neural network 93 and the six virtual monochromatic X-ray images $A_{11}$, $A_{12}$, $A_{13}$, $A_{15}$, $A_{16}$, and $A_{17}$ are output from the neural network 93.

Figure 8:
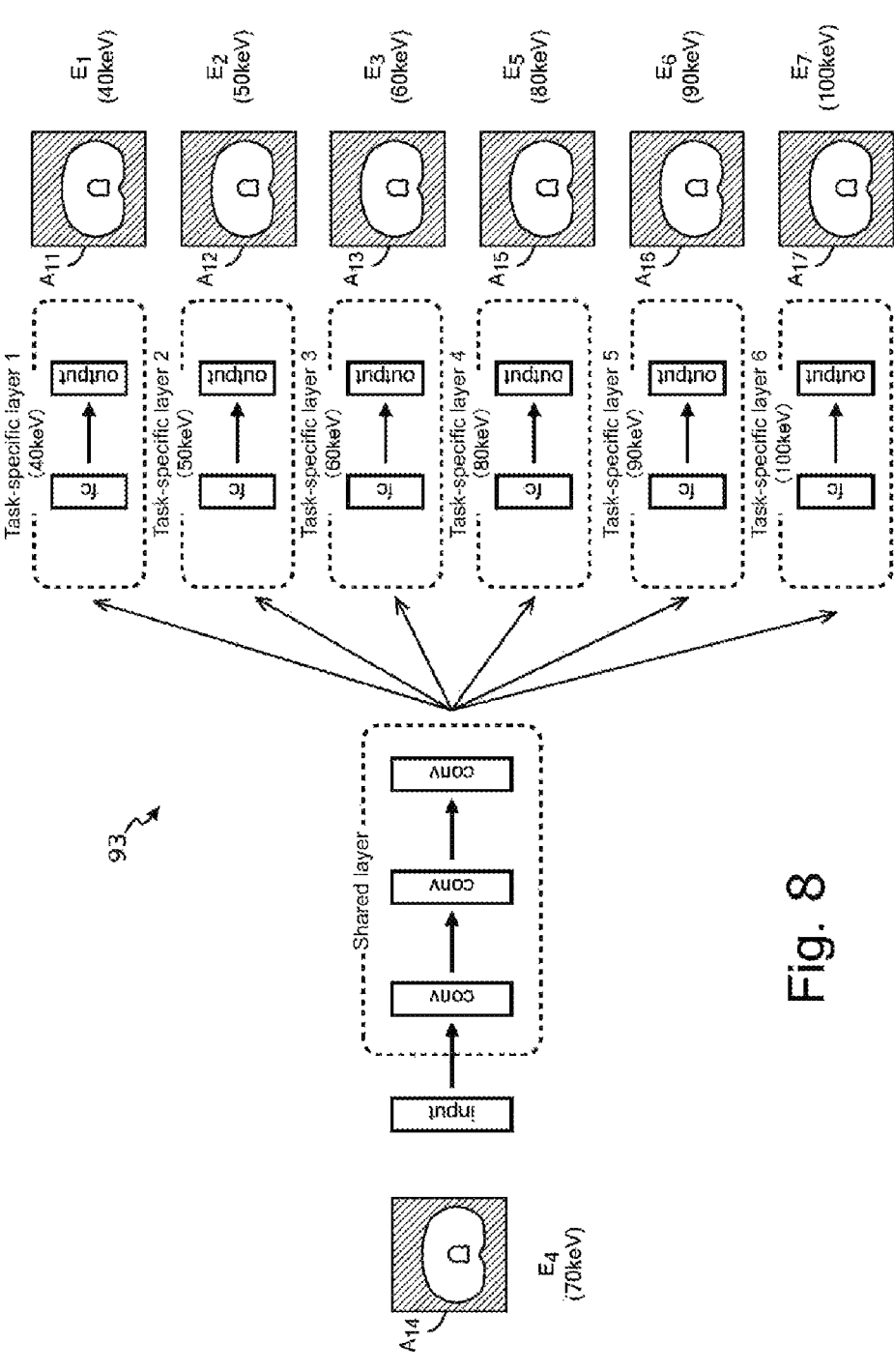
FIG. 8 is an explanatory diagram of the training method of the neural network 93 using a multi-task learning technique.

Furthermore, in Embodiment 1, the training device performs training of the neural network 93 using the multi-task learning technique (see FIG. 8). FIG. 8 is an explanatory diagram of the training method of the neural network 93 using the multi-task learning technique. Multi-task learning is a training method that allows a plurality of tasks to be learned simultaneously. In Embodiment 1, the neural network 93 has the shared layer and the plurality of task-specific layers 1 to 6.

The shared layer learns feature values of each site in the virtual monochromatic X-ray images $A_{11}$, $A_{12}$, $A_{13}$, $A_{14}$, $A_{15}$, $A_{16}$, and $A_{17}$ at the energy levels E1, E2, E3, E4, E5, E6, and E7. The feature values of each site are, for example, image resolution, image dynamic range, edge sharpness, and the like. The task-specific layers 1-6 learn how much to adjust the CT values of virtual monochromatic X-ray images of other energy levels (E1, E2, E3, E5, E6, and E7) based on the CT values of the virtual monochromatic X-ray image $A_{14}$ of the energy level E4.

The task-specific layer 1 is associated with the 40 (keV) virtual monochromatic X-ray image $A_{11}$. The task-specific layer 1 learns how much to adjust the CT value of the 40 (keV) virtual monochromatic X-ray image $A_{11}$, which is associated with task-specific layer 1, based on the CT value of the 70 (keV) virtual monochromatic X-ray image $A_{14}$.

The task-specific layer 2 is associated with the 50 (keV) virtual monochromatic X-ray image $A_{12}$. The task-specific layer 2 learns how much to adjust the CT value of the 50 (keV) virtual monochromatic X-ray image $A_{12}$, which is associated with task-specific layer 2, based on the CT value of the 70 (keV) virtual monochromatic X-ray image $A_{14}$.

The task-specific layer 3 is associated with the 60 (keV) virtual monochromatic X-ray image $A_{13}$. The task-specific layer 3 learns how much to adjust the CT value of the 60 (keV) virtual monochromatic X-ray image $A_{13}$, which is associated with task-specific layer 3, based on the CT value of the 70 (keV) virtual monochromatic X-ray image $A_{14}$.

The task-specific layer 4 is associated with the 80 (keV) virtual monochromatic X-ray image $A_{15}$. The task-specific layer 4 learns how much to adjust the CT value of the 80 (keV) virtual monochromatic X-ray image $A_{15}$, which is associated with task-specific layer 4, based on the CT value of the 70 (keV) virtual monochromatic X-ray image $A_{14}$.

The task-specific layer 5 is associated with the 90 (keV) virtual monochromatic X-ray image $A_{16}$. The task-specific layer 6 learns how much to adjust the CT value of the 90 (keV) virtual monochromatic X-ray image $A_{16}$, which is associated with task-specific layer 5, based on the CT value of the 70 (keV) virtual monochromatic X-ray image $A_{14}$.

The task-specific layer 6 is associated with the 100 (keV) virtual monochromatic X-ray image $A_{17}$. The task-specific layer 6 learns how much to adjust the CT value of the 100 (keV) virtual monochromatic X-ray image $A_{17}$, which is associated with task-specific layer 6, based on the CT value of the 70 (keV) virtual monochromatic X-ray image $A_{14}$. Thus, in the neural network 93, training is performed using the virtual monochromatic X-ray images $A_{11}$ to $A_{17}$ in the shared layer and task-specific layers 1 to 6.

Note that FIGS. 7 and 8 depict a case in which learning is performed in the neural network 93 using the virtual monochromatic X-ray images $A_{11}$ to $A_{17}$, but learning is also performed for other virtual monochromatic X-ray images in the same manner. Thus, the neural network 93 performs learning using the training data 91, creating the trained neural network 94. Note that in the training phase, a prescribed range of CT values may be intensively learned. For example, in a scan using a contrast agent, the CT value of the contrast agent is important for diagnosis, and therefore, the range of CT values of the contrast agent may be intensively learned. By determining the range of CT values to be intensively learned in this manner, it is possible to provide a trained neural network that can infer an image that is even more suitable for diagnostic purposes.

The trained neural network 94 is stored in the storage device 218 (see FIG. 2) of the CT system 100. Note that the trained neural network 94 may be stored on an external storage device accessible by the CT system 100. In Embodiment 1, the trained neural network 94 created as described above is used to infer a plurality of virtual monochromatic X-ray images having different energy levels. The flow of inferring a plurality of virtual monochromatic X-ray images using the trained neural network 94 is described below, with reference to the flow on the right side of FIG. 4.

Figure 9:
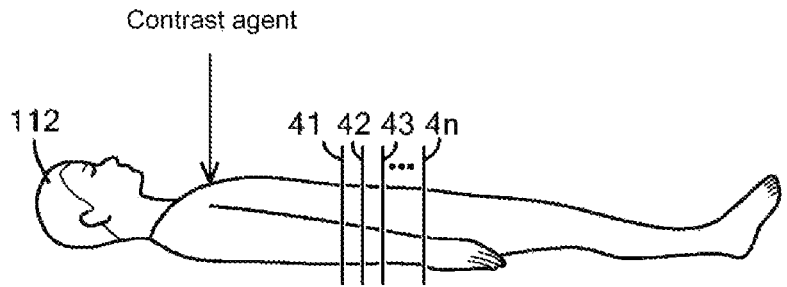
FIG. 9 is an explanatory diagram of the scan of the subject body.

At step ST1, a subject body scan is performed. Specifically, as depicted in FIG. 9, a contrast agent is injected into the subject body 112 and a contrast-enhanced CT scan is performed using the CT system 100 to obtain a contrast-enhanced image of the imaging site of the subject body 112. Herein, a scan is performed to acquire contrast-enhanced images of slices 41-4n set with respect to the imaging site of the subject body 112. Note that the tube voltage during scanning is 120 kVp. The data obtained from the scan is collected by the DAS 214 (see FIG. 2), and the collected data is transmitted to the computer 216 or image reconstruction unit 230.

Returning to FIG. 4, the description is continued. In step ST2, the processor of the computer 216 or image reconstructor 230 generates CT images 11 to 1n (CT image set 10) of the slices 41 to 4n (see FIG. 9) of the imaging site based on the data collected from the subject body in step ST1. In FIG. 4, only the CT image 11 is enlarged from the CT images 11 to 1*n*. After generating the CT images 11 to 1*n*, the flow proceeds to step ST3.

In step ST3, the processor of the computer 216 causes the trained neural network 94, based on each CT image, to infer the virtual monochromatic X-ray images of the energy levels E1=40 (keV), E2=50 (keV), E3=60 (keV), E5=80 (keV), E6=90 (keV), and E7=100 (keV). Specifically, in step ST3, the processor of the computer 216 first inputs the CT image 11 to the trained neural network 94 as an input image, and uses the trained neural network 94 to infer the virtual monochromatic X-ray images 21 to 26 of the energy levels E1=40 (keV), E2=50 (keV), E3=60 (keV), E5=80 (keV), E6=90 (keV), and E7=100 (keV). Therefore, the plurality of virtual monochromatic X-ray images 21 to 26 having different energy levels can be inferred for the CT image 11.

In the same manner below, the processor of the computer 216 inputs each additional CT images 12 to 1*n* to the trained neural network 94 as input images, and infers a plurality of virtual monochromatic X-ray images having different energy levels for each input image. Therefore, the plurality of virtual monochromatic X-ray images having different energy levels can be inferred for each of the CT images 11 to 1*n*. Note that for convenience of explanation, only the virtual monochromatic X-ray images 21 to 26 inferred for CT image 11 are depicted in FIG. 4, and the virtual monochromatic X-ray images inferred for the other CT images 12 to 1*n* are omitted. The operator displays the inferred virtual monochromatic X-ray images on the display part and checks each image. Thus, the flow depicted in FIG. 4 is completed.

In Embodiment 1, the trained neural network 94 is created in the training phase. In the training phase, a plurality of virtual monochromatic X-ray images generated based on dual energy CT data are prepared as training data, and the neural network 93 is caused to learn the training data to create the trained neural network 94. Specifically, virtual monochromatic X-ray images of the plurality of energy levels E1 to E7 are prepared, and the neural network 93 performs learning such that the virtual monochromatic X-ray image of the energy level E4 (=70 (keV)) is used as an input of the neural network 93, and the virtual monochromatic X-ray images of the other energy levels E1=40 (keV), E2=50 (keV), E3=60 (keV), E5=80 (keV), E6=90 (keV), and E7=100 (keV) are output from the neural network 93. Furthermore, the virtual monochromatic X-ray image of the energy level E4 (=70 (keV)) used as an input of the neural network 93 is a virtual monochromatic X-ray image of an energy level corresponding to the tube voltage of 120 kVp of the CT system 100 with single energy CT that is actually used to scan the subject body 112. Therefore, the CT image 11 obtained by single energy CT can be input to the trained neural network 94 to infer virtual monochromatic X-ray images of other energies (40 (keV), 50 (keV), 60 (keV), 80 (keV), 90 (keV), and 100 (keV)) having sufficient quality. Thus, in Embodiment 1, virtual monochromatic X-ray images of various energy levels can be inferred based on the CT images 11 generated from the CT system 100 with single energy CT. Therefore, even medical institutions having only CT systems with single energy CT can obtain virtual monochromatic X-ray images of optimal contrast for clinical purposes from a plurality of inferred virtual monochromatic X-ray images.

In Embodiment 1, the neural network 93 learns, in the shared layer, a feature value of a site in the virtual monochromatic X-ray image and, in the plurality of task-specific layers, how much to adjust the CT value of the virtual monochromatic X-ray image for the corresponding energy level, such that the trained neural network 94 that infers a plurality of virtual monochromatic x-ray images is created. In contrast, in the case of inferring the plurality of virtual monochromatic X-ray images, another possible method, different from the method of Embodiment 1, is to create a separate trained neural network for each virtual monochromatic X-ray image to be inferred. However, the method of creating the trained neural network 94 in Embodiment 1 is expected to increase the inference accuracy of a plurality of virtual monochromatic X-ray images compared to the method of creating a trained neural network for each virtual monochromatic X-ray image to be inferred. The reason is described below. Note that in describing the reason, the disadvantages of the method of creating a trained neural network for each virtual monochromatic X-ray image will be described, with reference to FIG. 10. Furthermore, after clarifying the disadvantages, the advantages of Embodiment 1 of the method of creating the trained neural network 94 will be described.

Figure 10:
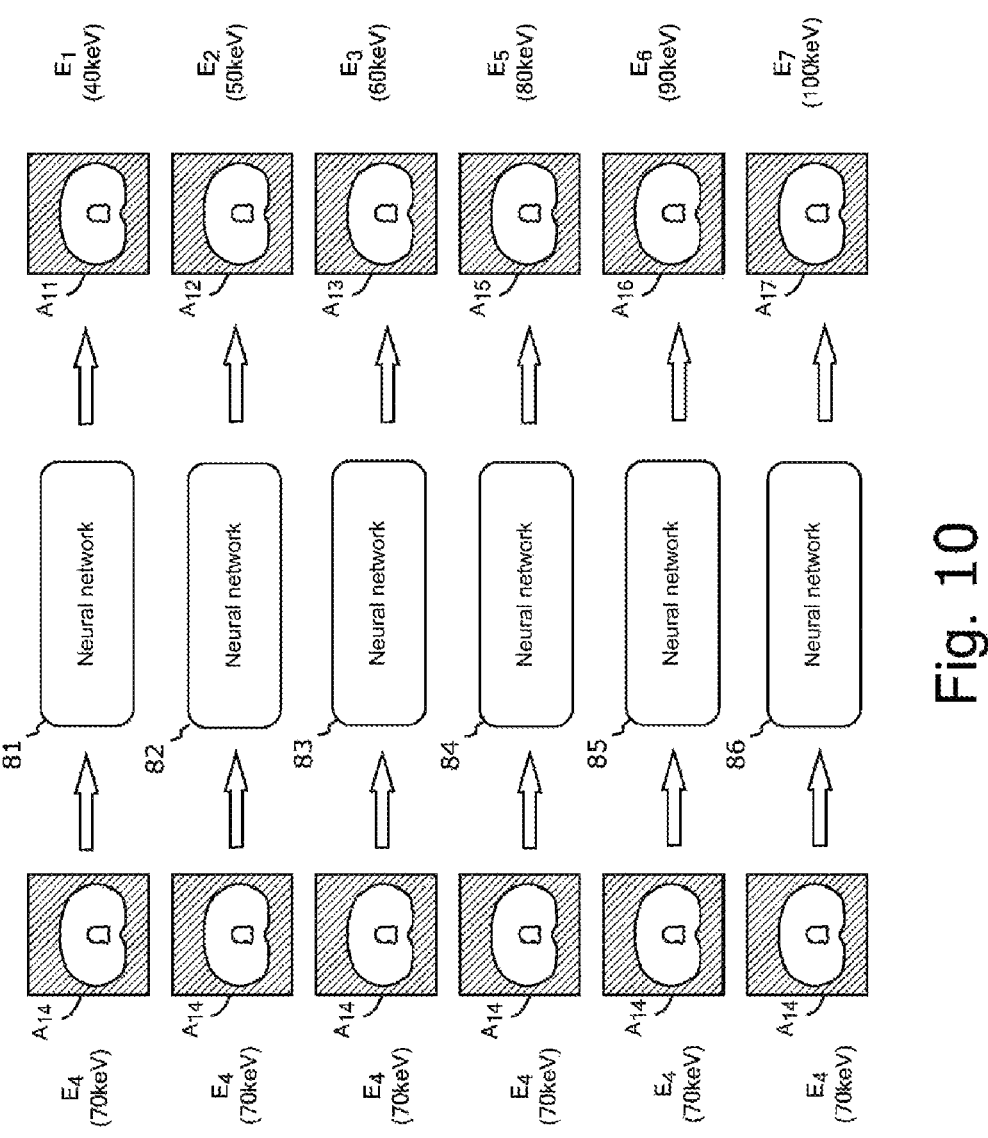
FIG. 10 is an explanatory diagram of a method of creating a trained neural network for each virtual monochromatic X-ray image.

FIG. 10 is an explanatory diagram of the method of creating a trained neural network for each virtual monochromatic X-ray image. In this method, the neural network performs learning for each virtual monochromatic x-ray image to be inferred. In FIG. 10, neural networks 81 to 86 are depicted. The neural networks 81 to 86 learn in the training phase as in the following (a) to (0.

(a) Neural network 81 performs learning such that the 40 (keV) virtual monochromatic X-ray image $A_{11}$ is inferred for the 70 (keV) virtual monochromatic X-ray image $A_{14}$.

(b) Neural network 82 performs learning such that the 50 (keV) virtual monochromatic X-ray image $A_{11}$ is inferred for the 70 (keV) virtual monochromatic X-ray image $A_{14}$.

(c) Neural network 83 performs learning such that the 60 (keV) virtual monochromatic X-ray image $A_{13}$ is inferred for the 70 (keV) virtual monochromatic X-ray image $A_{14}$.

(d) Neural network 84 performs learning such that the 80 (keV) virtual monochromatic X-ray image $A_{15}$ is inferred for the 70 (keV) virtual monochromatic X-ray image $A_{14}$.

(e) Neural network 85 performs learning such that the 90 (keV) virtual monochromatic X-ray image $A_{16}$ is inferred for the 70 (keV) virtual monochromatic X-ray image $A_{14}$.

(f) Neural network 86 performs learning such that the 100 (keV) virtual monochromatic X-ray image $A_{17}$ is inferred for the 70 (keV) virtual monochromatic X-ray image $A_{14}$.

Therefore, the neural networks 81 to 86 each independently learn the virtual monochromatic X-ray image of 70 (keV). Therefore, the neural networks 81 to 86 may have different learning results for the virtual monochromatic X-ray image of 70 (keV). Furthermore, the neural network 81 learns only virtual monochromatic X-ray images of two energy levels, namely, the virtual monochromatic X-ray image $A_{14}$ of 70 (keV) and the virtual monochromatic X-ray image $A_{11}$ of 40 (keV), and does not learn the virtual monochromatic X-ray images of other energy levels. Similarly, the other neural networks 82 to 86 also learn only virtual monochromatic X-ray images of two energy levels. Therefore, each of the neural networks 81 to 86 learns only two virtual monochromatic X-ray images of the virtual monochromatic X-ray images of 40 (keV), 50 (keV), 60 (keV), 70 (keV), 80 (keV), 90 (keV), and 100 (keV). As a result, the method in FIG. 10 may result in variations in inference results, making it difficult to infer reliable virtual monochromatic X-ray images.

On the other hand, the method of Embodiment 1 allows the shared layer of the neural network 93 (see FIG. 8) to learn a feature value of sites in the virtual monochromatic X-ray images of all energy levels, and thus consistency can be provided for the learning results of the virtual monochromatic X-ray images of each energy level. Furthermore, the task-specific layers 1 to 6 learn virtual monochromatic X-ray images based on consistent learning results obtained from the shared layer. Therefore, the inference accuracy of virtual monochromatic X-ray images can be improved.

In Embodiment 1, the subject body 112 is scanned with the CT system 100 with single energy CT. In general, in CT images acquired by single energy CT, it may be difficult to see significant differences between CT values of a contrast agent and soft tissue. Therefore, when contrast-enhanced imaging is performed on a subject body in whom only a thin density of the contrast agent can be injected (e.g., a subject body with kidney disease) using the CT system 100 with single energy CT, it is difficult to obtain a CT image in which the contrast agent is sufficiently highlighted, which may cause problems such as time consumed in image interpretation and re-imaging. In contrast, in Embodiment 1, a virtual monochromatic X-ray image at a low energy level (e.g., the virtual monochromatic X-ray image of 40 (keV)) that can highlight the contrast agent can be inferred based on CT images obtained by the CT system 100 with single energy CT. Therefore, it is possible to avoid problems such as a prolonged image interpretation time and re-imaging.

Note that in Embodiment 1, the virtual monochromatic X-ray image having the energy level of 70 (keV) is used as an input of the neural network 93 during the training phase. However, a virtual monochromatic X-ray image having an energy level different from 70 (keV) may be used as the input of the neural network 93. For example, if the CT system 100 uses other tube voltages instead of 120 kVp, a virtual monochromatic x-ray image having a different energy level than 70 (keV) can be used as the input of the neural network 93 to perform training. For example, if the tube voltage of the CT system 100 is 140 kVp instead of 120 kVp, a virtual monochromatic X-ray image of 75 (keV) can be used as the input of the neural network 93, since 140 kVp corresponds to an energy level of approximately 75 (keV). Therefore, if the tube voltage of the CT system 100 is 140 kVp, virtual monochromatic X-ray images with energy levels of 40 (keV), 50 (keV), 60 (keV), 70 (keV), 75 (keV), 80 (keV), 90 (keV), and 100 (keV), for example, can be prepared as training data. The neural network 93 can perform learning with the virtual monochromatic X-ray images, such that the virtual monochromatic X-ray image having an energy level of 75 (keV) is used as the input of the neural network 93, and virtual monochromatic X-ray images of other energies are output from the neural network 93.

Furthermore, if the tube voltage of the CT system 100 with single energy CT is 100 kVp, a virtual monochromatic X-ray image of 65 (keV) can be used as the input of the neural network 93, since 100 kVp corresponds to an energy level of approximately 65 (keV). Therefore, if the tube voltage of the CT system 100 is 100 kVp, virtual mono-chromatic X-ray images with energy levels of 40 (keV), 50 (keV), 60 (keV), 65 (keV), 70 (keV), 80 (keV), 90 (keV), and 100 (keV), for example, can be prepared as training data. The neural network 93 can perform learning with the virtual monochromatic X-ray images, such that the virtual monochromatic X-ray image having an energy level of 65 (keV) is used as the input of the neural network 93, and virtual monochromatic X-ray images of other energies are output from the neural network 93.

Furthermore, after inferring the virtual monochromatic X-ray images 21 to 26 in step ST3 (see FIG. 4), a region of interest may be set in the CT image 11 and a spectral curve corresponding to the region of interest may be created based on the CT values of the virtual monochromatic X-ray images 21 to 26. By creating the spectral curve, it is possible to perform material discrimination.

In Embodiment 1, the trained neural network 94 is created based on training data obtained from a contrast-enhanced CT scan. However, the present invention is not limited to the example of creating the trained neural network 94 based on training data obtained from a contrast-enhanced CT scan, and so long as a virtual monochromatic X-ray image can be inferred, a trained neural network obtained by a non-contrast-enhanced scan may be created.

While virtual monochromatic X-ray images at energy levels of 40 (keV), 50 (keV), 60 (keV), 80 (keV), 90 (keV), and 100 (keV) were inferred in Embodiment 1, Embodiment 2 describes an example provided with a function that allows the operator to select the inferred virtual monochromatic X-ray image. The operator first operates the operator console 220 (see FIG. 1) to display the mode selection screen on the display part 232. The operator console 220 inputs to the computer 216 a signal for causing the display part 232 to display the mode selection screen in response to the operation of the operator. The processor of computer 216 displays the mode selection screen on display part 232 in response to the signal from operator console 220 (see FIG. 11).

Figure 11:
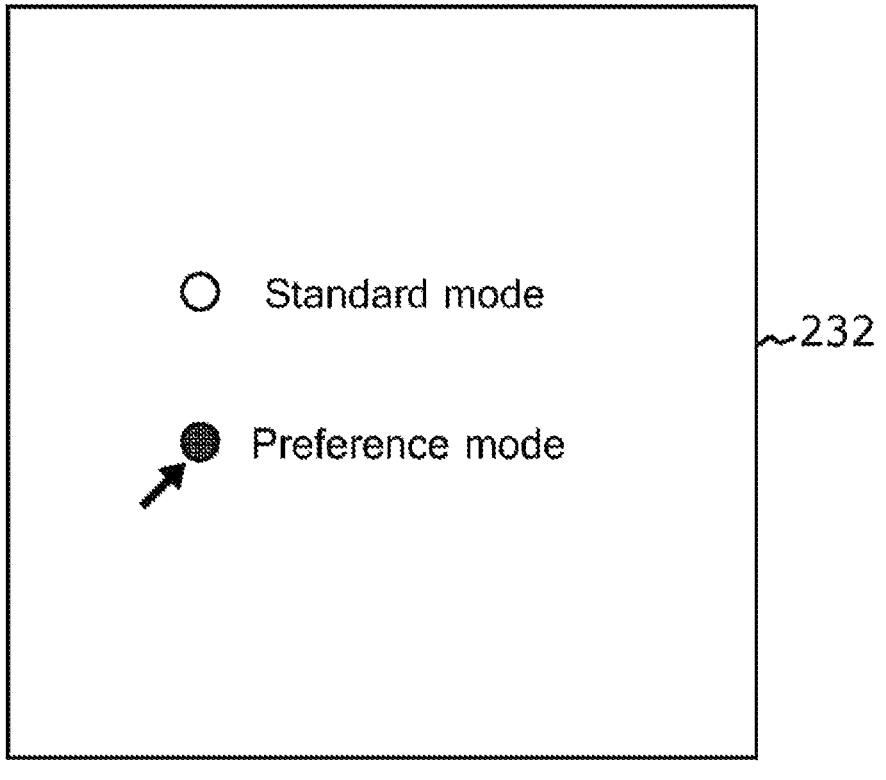
FIG. 11 is a diagram depicting an example of a mode selection screen.

FIG. 11 is a diagram depicting an example of the mode selection screen. The display part 232 displays a standard mode and preference mode. The mode selection screen is used to allow the operator to select one of either the standard mode or preference mode. The standard mode is a mode in which all virtual monochromatic X-ray images of 40 (keV), 50 (keV), 60 (keV), 80 (keV), 90 (keV), and 100 (keV) are inferred. On the other hand, the preference mode is a mode allowing the operator to select the virtual monochromatic X-ray image to be inferred from the virtual monochromatic X-ray images of 40 (keV), 50 (keV), 60 (keV), 80 (keV), 90 (keV), and 100 (keV).

The operator can operate the operator console 220 and select the standard mode or preference mode. When the operator operates the operator console 220 such that the standard mode is selected, the operator console 220 inputs a signal to the computer 216 to select the standard mode in response to the operation of the operator. The processor of the computer 216 sets an inference condition such that the virtual monochromatic X-ray images of all energy levels, namely, 40 (keV), 50 (keV), 60 (keV), 80 (keV), 90 (keV), and 100 (keV), are all inferred in response to the signal from the operator console 220.

On the other hand, if the operator desires to select a virtual monochromatic X-ray image to be inferred, the operator can operate the operator console 220 to select the preference mode. When the operator operates the operator console 220 such that the preference mode is selected, the operator console 220 inputs a signal to the computer 216 to select the preference mode in response to the operation of the operator. The processor of the computer 216 controls the display part 232 such that, in response to the signal from operator console 220, an energy level selection screen is displayed to allow the operator to select the energy level of the virtual monochromatic X-ray image to be inferred (see FIG. 12).

Figure 12:
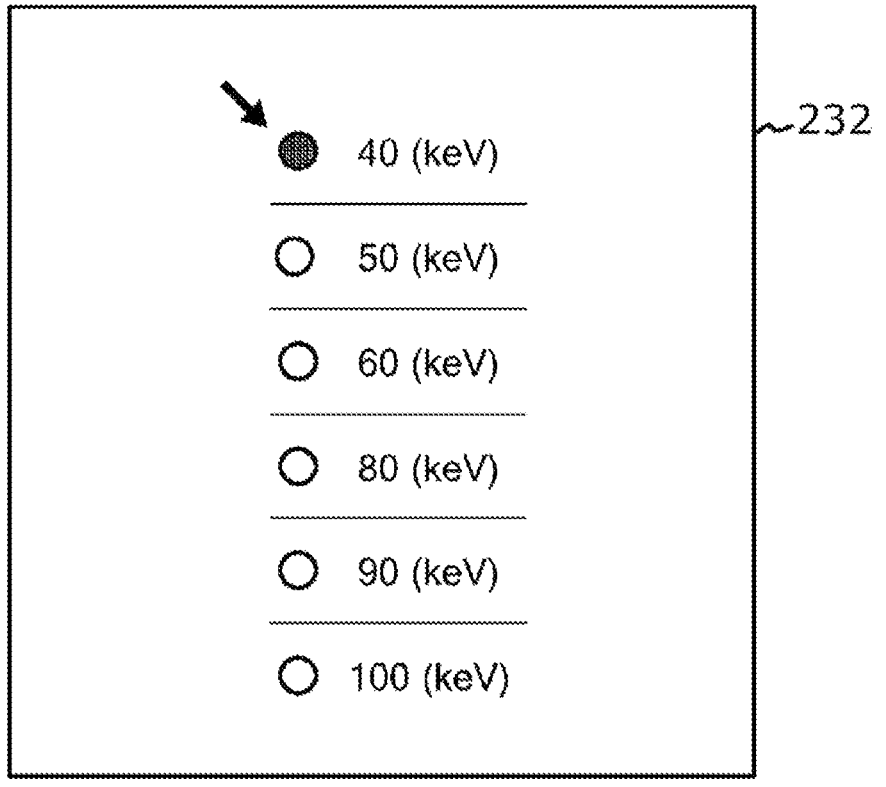
FIG. 12 is a diagram depicting an example of an energy level selection screen.

FIG. 12 is a diagram depicting an example of the energy level selection screen. The display part 232 displays 40

(keV), 50 (keV), 60 (keV), 80 (keV), 90 (keV), and 100 (keV) as energy levels. The operator can select which energy level of the virtual monochromatic X-ray image to be inferred from 40 (keV), 50 (keV), 60 (keV), 80 (keV), 90 (keV), and 100 (keV), depending on the diagnostic purpose or the like. For example, when performing imaging using a contrast agent, the operator may desire to obtain a virtual monochromatic X-ray image at a low energy level because a virtual monochromatic X-ray image at a low energy level can further highlight the contrast agent as compared to a virtual monochromatic X-ray image at a high energy level. In this case, the operator can select, for example, the virtual monochromatic X-ray image of 40 (keV) as a low energy level virtual monochromatic X-ray image, as depicted in FIG. 12. The virtual monochromatic X-ray image of 40 (keV) is particularly suitable for observing sites such as soft tissue and the like, where the inflow of the contrast agent is less than that of blood vessels.

On the other hand, the amount of contrast agent flowing through the blood vessels is large. Therefore, the brightness of the contrast agent flowing through the blood vessels is highlighted too brightly in the virtual monochromatic X-ray image of 40 (keV), and some operators may feel that the blood vessels are visually difficult to see. Therefore, some operators may prefer a virtual monochromatic X-ray image having an energy level of 50 (keV), which is higher than the virtual monochromatic X-ray image of 40 (keV), if they desire to acquire an image in which blood vessels are easily visible.

Figure 13:
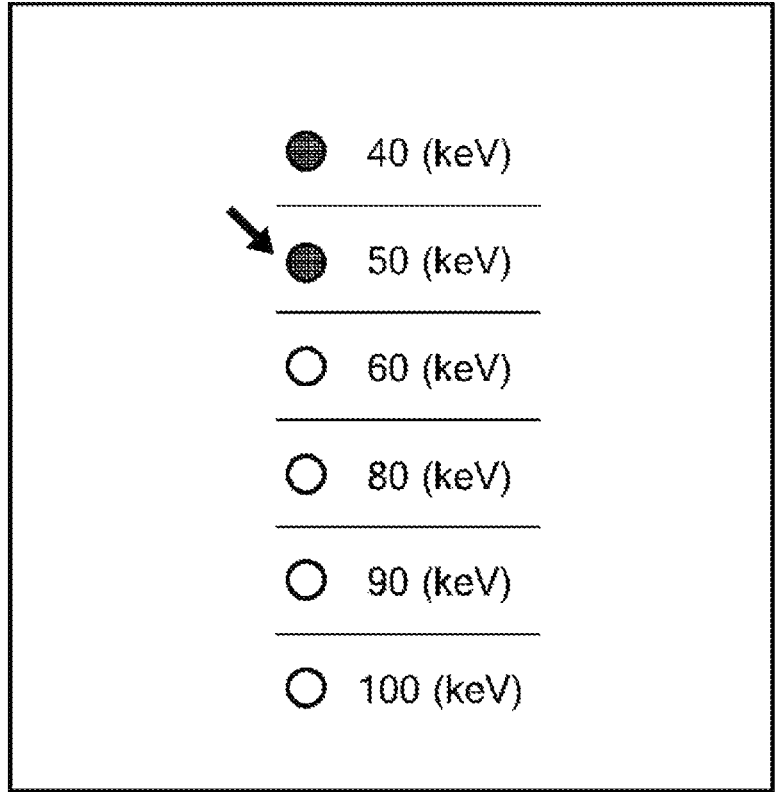
FIG. 13 is a diagram depicting a screen where both 40 (keV) and 50 (keV) energy levels are selected.

Therefore, if the operator desires to satisfy both the requirement of highlighting the contrast agent flowing into the soft tissue and the requirement of making the blood vessels more visible, it is desirable to have the operator infer the virtual monochromatic x-ray image of 40 (keV) and the virtual monochromatic x-ray image of 50 (keV). In this case, the operator can select both 40 (keV) and 50 (keV), as depicted in FIG. 13. By inferring the virtual monochromatic X-ray images of 40 (keV) and 50 (keV), the operator can preferentially refer to the virtual monochromatic X-ray image of 40 (keV) for soft tissue and the virtual monochromatic X-ray image of 50 (keV) for blood vessels, thus allowing the operator to acquire images according to the clinical purpose. Furthermore, the virtual monochromatic X-ray images of 60 (keV), 80 (keV), 90 (keV), and 100 (keV), which are not needed for diagnosis, are not inferred, thus reducing the inference phase time.

Figure 14:
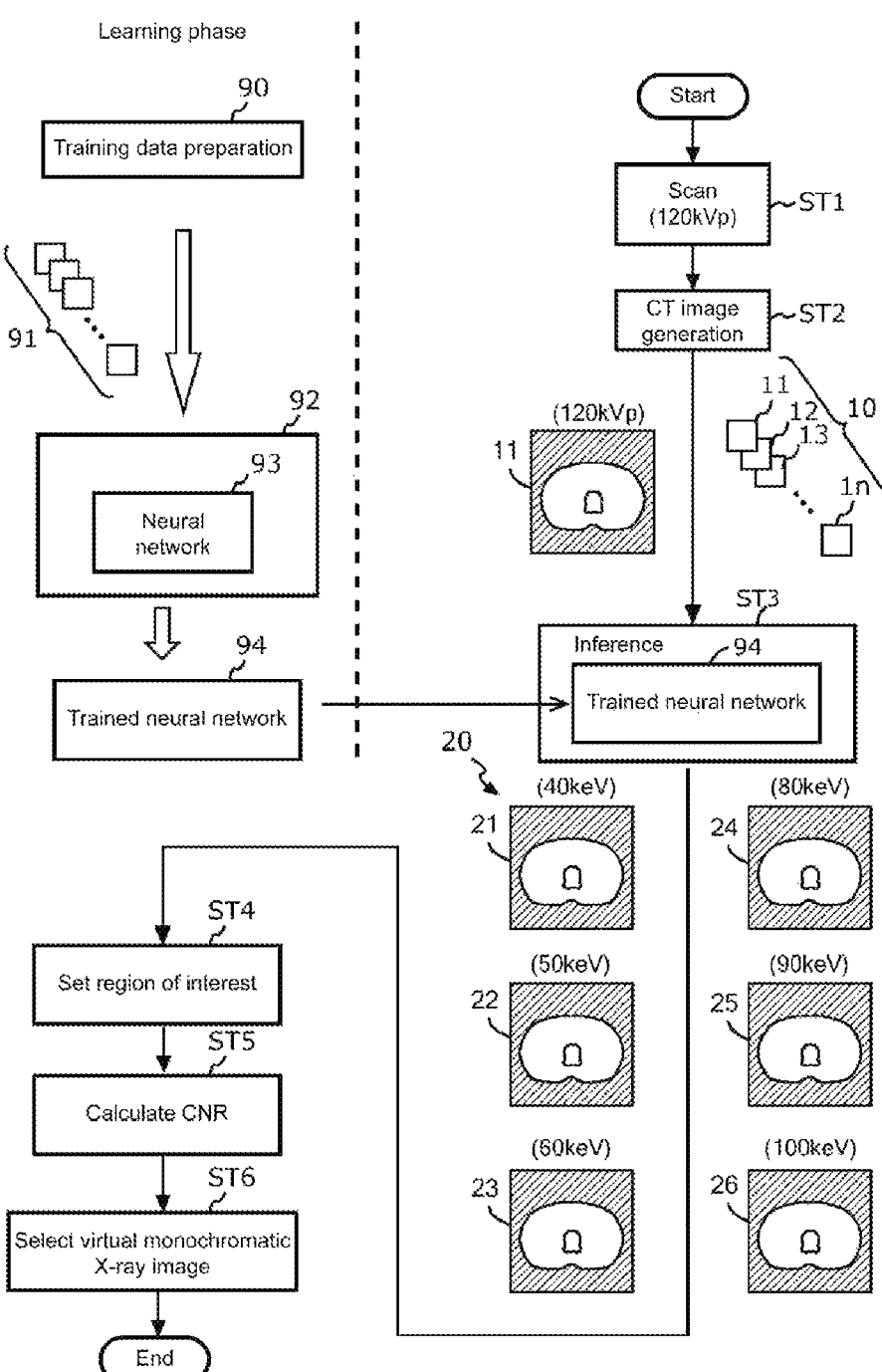
FIG. 14 is a flowchart performed in Embodiment 3.

Embodiment 3 described an example of presenting to the operator a virtual monochromatic X-ray image having an optimal contrast-to-noise ratio CNR from the inferred virtual monochromatic X-ray images of 40 (keV), 50 (keV), 60 (keV), 80 (keV), 90 (keV), and 100 (keV). An example of presenting this image to the operator is described below. FIG. 14 is a flowchart performed in Embodiment 3. Since the training phase and steps ST1 to ST3 are the same as the flow of Embodiment 1, a detailed description is omitted, and steps ST4 to ST6 are mainly described.

Figure 15:
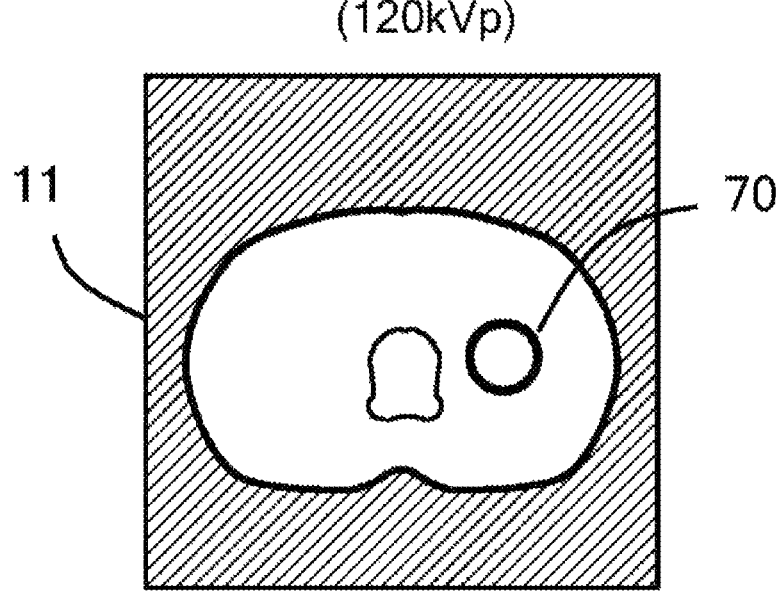
FIG. 15 is a diagram depicting an example of a region of interest.

In step ST4, the operator sets a region of interest on the CT image 11. FIG. 15 is a diagram depicting an example of the region of interest. The operator operates the operator console 220 and inputs a signal to set the region of interest on the CT image 11. The processor of the computer 216 sets a region of interest 70 on the CT image 11 in response to the signal from the operator console 220. After the region of interest 70 is set, the flow proceeds to step ST5.

Figure 16:
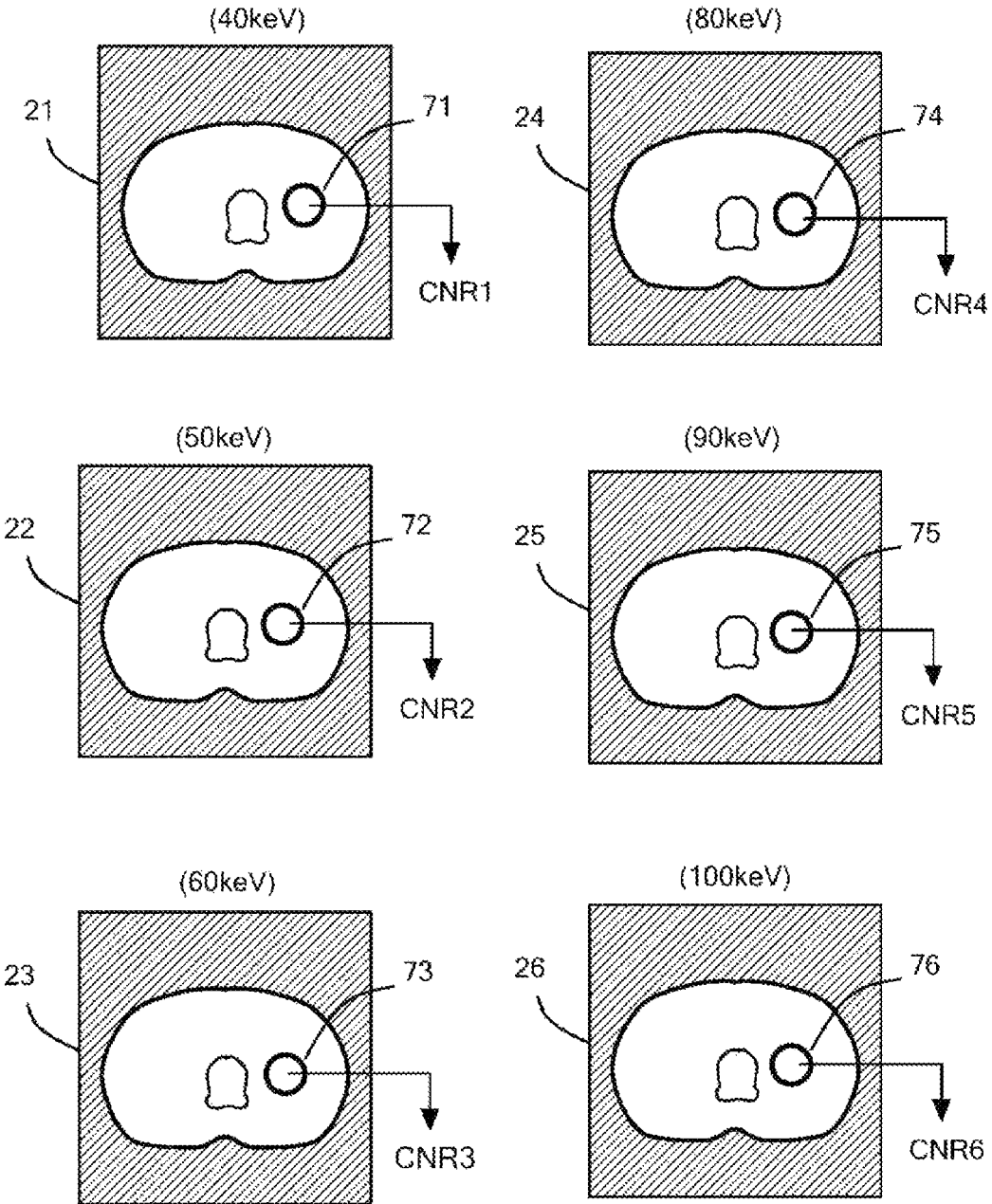
FIG. 16 is a diagram depicting a CNR calculated for each virtual monochromatic X-ray image.

In step ST5, a CNR is calculated for each virtual monochromatic X-ray image. FIG. 16 is a diagram depicting the CNR calculated for each virtual monochromatic X-ray image. The processor of the computer 216 specifies a region 71 corresponding to the region of interest 70 for the inferred virtual monochromatic X-ray image 21. Furthermore, the CNR (=CNR1) of the virtual monochromatic X-ray image 21 is calculated based on a pixel value in the region 71. In the same manner, regions 72, 73, 74, 75, and 76 corresponding to the region of interest 70 are specified for the other virtual monochromatic X-ray images 22, 23, 24, 25, and 26. Furthermore, the CNR2 to CNR6 of the virtual monochromatic X-ray images 22 to 26 are calculated based on pixel values in the regions 72 to 76. After the CNR is calculated, the flow proceeds to step ST6.

In step ST6, the processor of the computer 216 selects the virtual monochromatic X-ray image with the largest CNR from the virtual monochromatic X-ray images 21 to 26 based on the calculated CNR1 to CNR6. The selected virtual monochromatic X-ray image is displayed on the display part. The flow is thus completed. In Embodiment 3, the virtual monochromatic X-ray image with the maximum CNR is displayed. Therefore, from the inferred virtual monochromatic X-ray images, it is possible to display an image suitable for interpreting the region of interest.

As described above, according to the Embodiment 1 to Embodiment 3, a plurality of virtual monochromatic X-ray images having different energy levels can be inferred from a CT image obtained by single energy CT. Note that in order to confirm the quality of the virtual monochromatic X-ray images inferred by the technique of the present invention, a virtual monochromatic X-ray image was inferred using a trained neural network created by the technique of the present invention. The following is a description of an actually inferred virtual monochromatic X-ray image.

Figure 17:
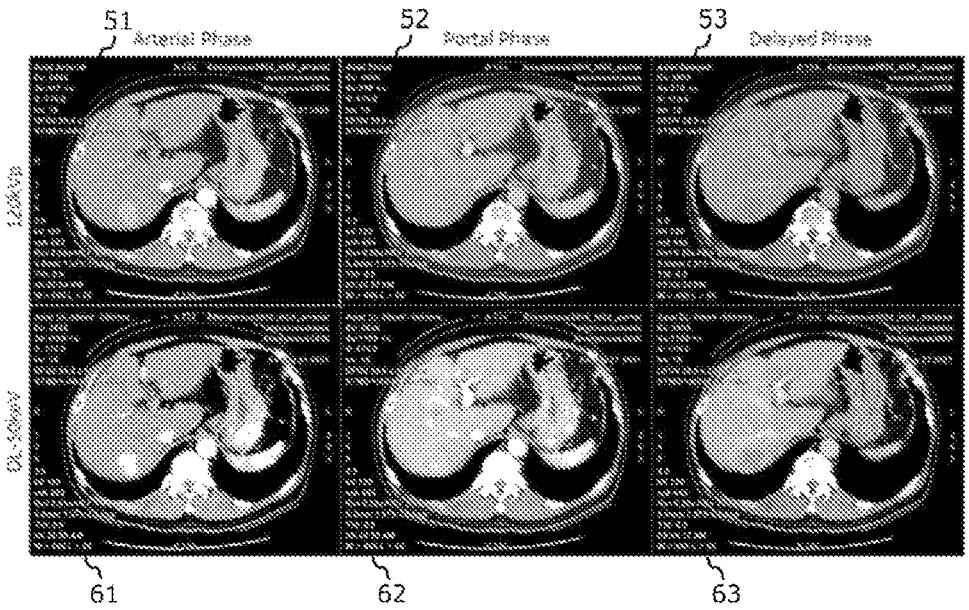
FIG. 17 is a diagram depicting actually inferred virtual monochromatic X-ray images.

FIG. 17 is a diagram depicting the actually inferred virtual monochromatic X-ray images. The top row of FIG. 17 depicts, for comparison, a CT image 51 of an arterial phase, CT image 52 of a venous phase, and CT image 53 of a delayed phase generated by a single energy CT at 120 kVp. Furthermore, the bottom row of FIG. 17 depicts a virtual monochromatic X-ray image 61 of 50 (keV) in the arterial phase, virtual monochromatic X-ray image 62 of 50 (keV) in the venous phase, and virtual monochromatic X-ray image 63 of 50 (keV) in the delayed phase, inferred by the technique of the present invention. A comparison of both images shows that the contrast agent in the virtual monochromatic X-ray image generated by the technique of the present invention is highlighted.

What is claimed is:

1. A device, comprising one or more processors for performing an operation, the operation including: inputting a CT image generated based on single energy CT data collected from a subject body into a trained neural network, the trained neural network being generated by a neural network performing learning using training data in a training phase, the training data including a plurality of virtual monochromatic X-ray images generated based on dual energy CT data and having mutually different energy levels, the plurality of virtual monochromatic X-ray images including a first virtual monochromatic X-ray image with an energy level corresponding to a tube voltage of a CT system collecting single energy CT data and a first set of two or more virtual monochromatic X-ray images having mutually different energy levels, and in the training phase, the neural network performing learning with the training data such that the first virtual monochromatic X-ray image is used as input to the neural network and the first set of two or more virtual monochromatic X-ray images are output from the neural network; and causing the trained neural network to infer a second set of a plurality of two or more virtual monochromatic X-ray images having different energy levels based on an input CT image, wherein the trained neural network is trained using a multi-task learning technique and includes a shared layer and a plurality of task-specific layers, wherein each task-specific layer is associated with a virtual monochromatic X-ray image having a different energy level than the first virtual monochromatic X-ray image.

2. The device according to claim 1, wherein the neural network performs learning using the training data using a multi-task learning technique, such that the trained neural network is created.

3. The device according to claim 1, wherein the neural network includes a shared layer and a plurality of task-specific layers, the shared layer learns a feature value of each site in the plurality of virtual monochromatic X-ray images, each task-specific layer is associated with a virtual monochromatic X-ray image having a different energy level than the first virtual monochromatic X-ray image of the plurality of virtual monochromatic X-ray images, and each of the task-specific layers learns how much to adjust a CT value of the virtual monochromatic X-ray image associated with each of the task-specific layers based on a CT value of the first virtual monochromatic X-ray image.

4. The device according to claim 1, wherein each of the first set of two or more virtual monochromatic X-ray images is an actual virtual monochromatic X-ray image obtained by scanning a patient or a pre-processed virtual monochromatic X-ray image obtained by performing a prescribed pre-processing with respect to the actual virtual monochromatic X-ray image.

5. The device according to claim 1, wherein each of the first set of two or more virtual monochromatic X-ray images and the CT image is an image obtained by performing a scan using a contrast agent.

6. A CT system for collecting single energy CT data, comprising: an X-ray tube to which a prescribed tube voltage is applied; and one or more processors, wherein the one or more processors performs an operation, the operation including: generating a CT image based on single energy CT data collected from a subject body, inputting the CT image to a trained neural network, the trained neural network being generated by a neural network performing learning using training data in a training phase, the training data including a plurality of virtual monochromatic X-ray images generated based on dual energy CT data and having mutually different energy levels, the plurality of virtual monochromatic X-ray images including a first virtual monochromatic X-ray image with an energy level corresponding to the prescribed tube voltage and a first set of two or more virtual monochromatic X-ray images having mutually different energy levels, and in the training phase, the neural network performing learning with the training data such that the first virtual monochromatic X-ray image is used as input to the neural network and the first set of two or more virtual monochromatic X-ray images are output from the neural network; and causing the trained neural network to infer a second set of two or more virtual monochromatic X-ray images having different energy levels based on an input CT image, wherein the trained neural network is trained using a multi-task learning technique and includes a shared layer and a plurality of task-specific layers, wherein each task-specific layer is associated with a virtual monochromatic X-ray image having a different energy level than the first virtual monochromatic X-ray image.

7. The CT system according to claim 6, wherein the neural network includes a shared layer and a plurality of task-specific layers, the shared layer learns a feature value of each site in the plurality of virtual monochromatic X-ray images, each task-specific layer is associated with a virtual monochromatic X-ray image having a different energy level than the first virtual monochromatic X-ray image of the plurality of virtual monochromatic X-ray images, and each of the task-specific layers learns how much to adjust a CT value of the virtual monochromatic X-ray image associated with each of the task-specific layers based on a CT value of the first virtual monochromatic X-ray image.

8. The CT system according to claim 6, configured so as to perform:

a first mode in which all of the second set of two or more virtual monochromatic X-ray images are inferred; and a second mode in which an operator can select an inferred virtual monochromatic X-ray image from the second set of two or more virtual monochromatic X-ray images.

9. The CT system according to claim 8, comprising:

a display part, wherein the one or more processors causes the display part to display a mode selection screen to allow the operator to select one of the first mode and second mode.

10. The CT system according to claim 9, further comprising:

an operator console; and a computer coupled to the operator console and the display part and including one or more processors, wherein the operator console inputs to the computer a signal for causing the display part to display the mode selection screen in response to an operation of the operator, and a processor of the computer causes the display part to display the mode selection screen in response to the signal from the operator console.

11. The CT system according to claim 10, wherein when the operator console inputs a signal selecting the second mode in response to an operation of the operator, the processor of the computer causes the display part to display a screen to allow the operator to select an energy level of an inferred virtual monochromatic X-ray image in response to the signal from the operator console.

12. The CT system according to claim 9, wherein the one or more processors performs an operation, the operation including:

setting a region of interest on the CT image;

specifying a region corresponding to the region of interest with respect to the virtual monochromatic X-ray images included in the second set of two or more virtual monochromatic X-ray images;

calculating a CNR of the virtual monochromatic X-ray images based on a pixel value within the specified region with respect to the virtual monochromatic X-ray images;

selecting a virtual monochromatic X-ray image from the second set of two or more virtual monochromatic X-ray images based on the CNR of the virtual monochromatic X-ray images; and causing the display part to display the selected virtual monochromatic X-ray image.

13. A method of creating a trained neural network, comprising the step of a neural network performing learning using training data, the training data including a plurality of virtual monochromatic X-ray images generated based on dual energy CT data and having mutually different energy levels, the plurality of virtual monochromatic X-ray images including a first virtual monochromatic X-ray image with an energy level corresponding to a tube voltage of a CT system collecting single energy CT data and a first set of two or more virtual monochromatic X-ray images having mutually different energy levels, and the neural network performing learning with the training data such that the first virtual monochromatic X-ray image is used as input to the neural network and the first set of two or more virtual monochromatic X-ray images are output from the neural network, wherein the trained neural network is trained using a multi-task learning technique and includes a shared layer and a plurality of task-specific layers, wherein each task-specific layer is associated with a virtual monochromatic X-ray image having a different energy level than the first virtual monochromatic X-ray image.

14. The method according to claim 13, wherein the neural network includes a shared layer and a plurality of task-specific layers, the shared layer learns a feature value of each site in the plurality of virtual monochromatic X-ray images, each task-specific layer is associated with a virtual monochromatic X-ray image having a different energy level than the first virtual monochromatic X-ray image of the plurality of virtual monochromatic X-ray images, and each of the task-specific layers learns how much to adjust a CT value of the virtual monochromatic X-ray image associated with each of the task-specific layers based on a CT value of the first virtual monochromatic X-ray image.

15. The device according to claim 1, wherein the shared layer learns a feature value of each site in the plurality of virtual monochromatic X-ray images.

16. The device according to claim 1, wherein each of the task-specific layers learns how much to adjust a CT value of the virtual monochromatic X-ray image associated with each of the task-specific layers based on a CT value of the first virtual monochromatic X-ray image.

* * * * *